(12) United States Patent
Mason

(10) Patent No.: US 6,413,266 B1
(45) Date of Patent: Jul. 2, 2002

(54) TICK REMOVING DEVICE

(76) Inventor: Thomas A. Mason, 14621 Bowman Rd., Auburn, CA (US) 95602

( * ) Notice: Subject to any disclaimer, the term of this patent is extended or adjusted under 35 U.S.C. 154(b) by 0 days.

(21) Appl. No.: 09/895,890

(22) Filed: Jun. 29, 2001

(51) Int. Cl.[7] ............................................. A61B 17/50
(52) U.S. Cl. ..................................... 606/210; 606/131
(58) Field of Search ............................... 606/131, 210; 294/99.2

(56) References Cited

U.S. PATENT DOCUMENTS

| | | | |
|---|---|---|---|
| 220,390 A | * 10/1879 | Koska | 606/210 |
| 981,354 A | * 1/1911 | Anderson | 606/210 |
| 1,386,436 A | * 8/1921 | Smith | 606/210 |
| 1,837,277 A | * 12/1931 | Lund | 606/210 |
| 4,213,460 A | 7/1980 | Weiner | |
| 4,303,268 A | 12/1981 | Davidson | |
| 4,442,837 A | 4/1984 | Keatley | |
| 4,852,929 A | * 8/1989 | Shafer | 606/210 |
| 4,976,718 A | 12/1990 | Daniell | |
| 5,002,323 A | 3/1991 | Idsund | |
| 5,116,347 A | * 5/1992 | Butler | 606/210 |
| D388,859 S | 1/1998 | Carroll | |
| 5,868,787 A | * 2/1999 | Kim | 606/210 |

FOREIGN PATENT DOCUMENTS

FR      2483770    * 12/1981 ................. 606/131

* cited by examiner

*Primary Examiner*—Paul J. Hirsch

(57) ABSTRACT

A tick removing device includes a body member that includes a fulcrum portion and a pair arms. Each of the arms has a main portion that is coupled to the fulcrum portion. The head portion of each of the arms is for engaging a portion of a body of the tick. A distance between the head portion of each of the arms increases when a gap between the main portions of each of the arms is decreased by pressure for the fingers of the user. The head of one of the arms abuts the head portion of the other of the arms when pressure from the fingers on the main portion of each of the arms is released such that the head portion of each of the arms is for cooperatively securing the body member to the tick.

4 Claims, 4 Drawing Sheets

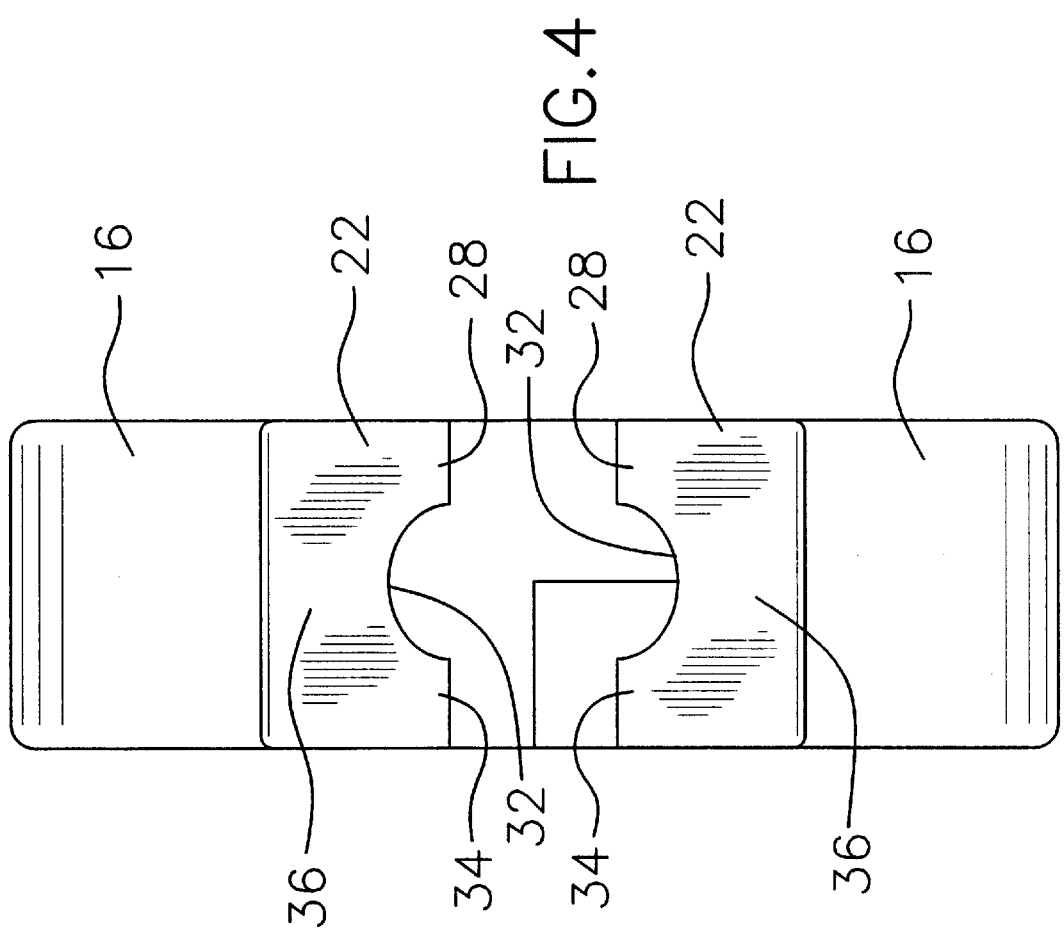

TICK REMOVING DEVICE

BACKGROUND OF THE INVENTION

1. Field of the Invention

The present invention relates to tick removing devices and more particularly pertains to a new tick removing device for allowing a user to efficiently and completely remove ticks from the skin of a pet. The present invention could also be used to remove ticks from humans.

2. Description of the Prior Art

The use of tick removing devices is known in the prior art. More specifically, tick removing devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,303,268; 4,442,837; 4,967,718; 4,213,460; 5,002,323; and U.S. Pat. No. Des. 388,859.

While these devices fulfill their respective, particular objectives and requirements, the aforementioned patents do not disclose a new tick removing device. The inventive device includes a body member that includes a fulcrum portion and a pair arms. Each of the arms has a main portion that is coupled to the fulcrum portion. One of the arms is positioned opposite from the other of the arms. The main portion of each of the arms is adapted for engaging a finger of a user. Each of the arms has a free end. The free end of one of the arms crosses over the free end of the other of the arms. Each of the arms has a head portion. The head portion of each of the arms is adapted for engaging a portion of a body of the tick. A distance between the head portion of each of the arms increases when a gap between the main portions of each of the arms is decreased by pressure for the fingers of the user. The head of one of the arms abuts the head portion of the other of the arms when pressure from the fingers on the main portion of each of the arms is released such that the head portion of each of the arms is adapted for cooperatively securing the body member to the tick when the tick is to be removed from the host.

In these respects, the tick removing device according to the present invention substantially departs from the conventional concepts and designs of the prior art, and in so doing provides an apparatus primarily developed for the purpose of allowing a user to efficiently and completely remove ticks from the skin of a pet. The present invention could also be used to remove ticks from humans.

SUMMARY OF THE INVENTION

In view of the foregoing disadvantages inherent in the known types of tick removing devices now present in the prior art, the present invention provides a new tick removing device construction wherein the same can be utilized for allowing a user to efficiently and completely remove ticks from the skin of a pet. The present invention could also be used to remove ticks from humans.

The general purpose of the present invention, which will be described subsequently in greater detail, is to provide a new tick removing device apparatus and method which has many of the advantages of the tick removing devices mentioned heretofore and many novel features that result in a new tick removing device which is not anticipated, rendered obvious, suggested, or even implied by any of the prior art tick removing devices, either alone or in any combination thereof.

To attain this, the present invention generally comprises a body member that includes a fulcrum portion and a pair arms. Each of the arms has a main portion that is coupled to the fulcrum portion. One of the arms is positioned opposite from the other of the arms. The main portion of each of the arms is adapted for engaging a finger of a user. Each of the arms has a free end. The free end of one of the arms crosses over the free end of the other of the arms. Each of the arms has a head portion. The head portion of each of the arms is adapted for engaging a portion of a body of the tick. A distance between the head portion of each of the arms increases when a gap between the main portions of each of the arms is decreased by pressure for the fingers of the user. The head of one of the arms abuts the head portion of the other of the arms when pressure from the fingers on the main portion of each of the arms is released such that the head portion of each of the arms is adapted for cooperatively securing the body member to the tick when the tick is to be removed from the host.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new tick removing device apparatus and method which has many of the advantages of the tick removing devices mentioned heretofore and many novel features that result in a new tick removing device which is not anticipated, rendered obvious, suggested, or even implied by any of the prior art tick removing devices, either alone or in any combination thereof.

It is another object of the present invention to provide a new tick removing device, which may be easily and efficiently manufactured and marketed.

It is a further object of the present invention to provide a new tick removing device, which is of a durable and reliable construction.

An even further object of the present invention is to provide a new tick removing device which is susceptible of a low cost of manufacture with regard to both materials and labor, and which accordingly is then susceptible of low prices of sale to the consuming public, thereby making such tick removing device economically available to the buying public.

Still yet another object of the present invention is to provide a new tick removing device, which provides in the apparatuses and methods of the prior art some of the advantages thereof, while simultaneously overcoming some of the disadvantages normally associated therewith.

Still another object of the present invention is to provide a new tick removing device for allowing a user to efficiently and completely remove ticks from the skin of a pet. The present invention could also be used to remove ticks from humans.

Yet another object of the present invention is to provide a new tick removing device, which includes a body member that includes a fulcrum portion and a pair arms. Each of the arms has a main portion that is coupled to the fulcrum portion. One of the arms is positioned opposite from the other of the arms. The main portion of each of the arms is adapted for engaging a finger of a user. Each of the arms has a free end. The free end of one of the arms crosses over the free end of the other of the arms. Each of the arms has a head portion. The head portion of each of the arms is adapted for engaging a portion of a body of the tick. A distance between the head portion of each of the arms increases when a gap between the main portions of each of the arms is decreased by pressure for the fingers of the user. The head of one of the arms abuts the head portion of the other of the arms when pressure from the fingers on the main portion of each of the arms is released such that the head portion of each of the arms is adapted for cooperatively securing the body member to the tick when the tick is to be removed from the host.

Still yet another object of the present invention is to provide a new tick removing device that enable the user to remove a tick without leaving the head of the tick embedded in the skin. It would also firmly grip the insect, thus allowing it to be easily placed in a bag or plastic vile for later analysis.

Even still another object of the present invention is to provide a new tick removing device that be compact, lightweight and inexpensive. The present invention could be used on animals as well as humans.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is an end view of the present invention.

DESCRIPTION OF THE PREFERRED EMBODIMENT

Figure 1:
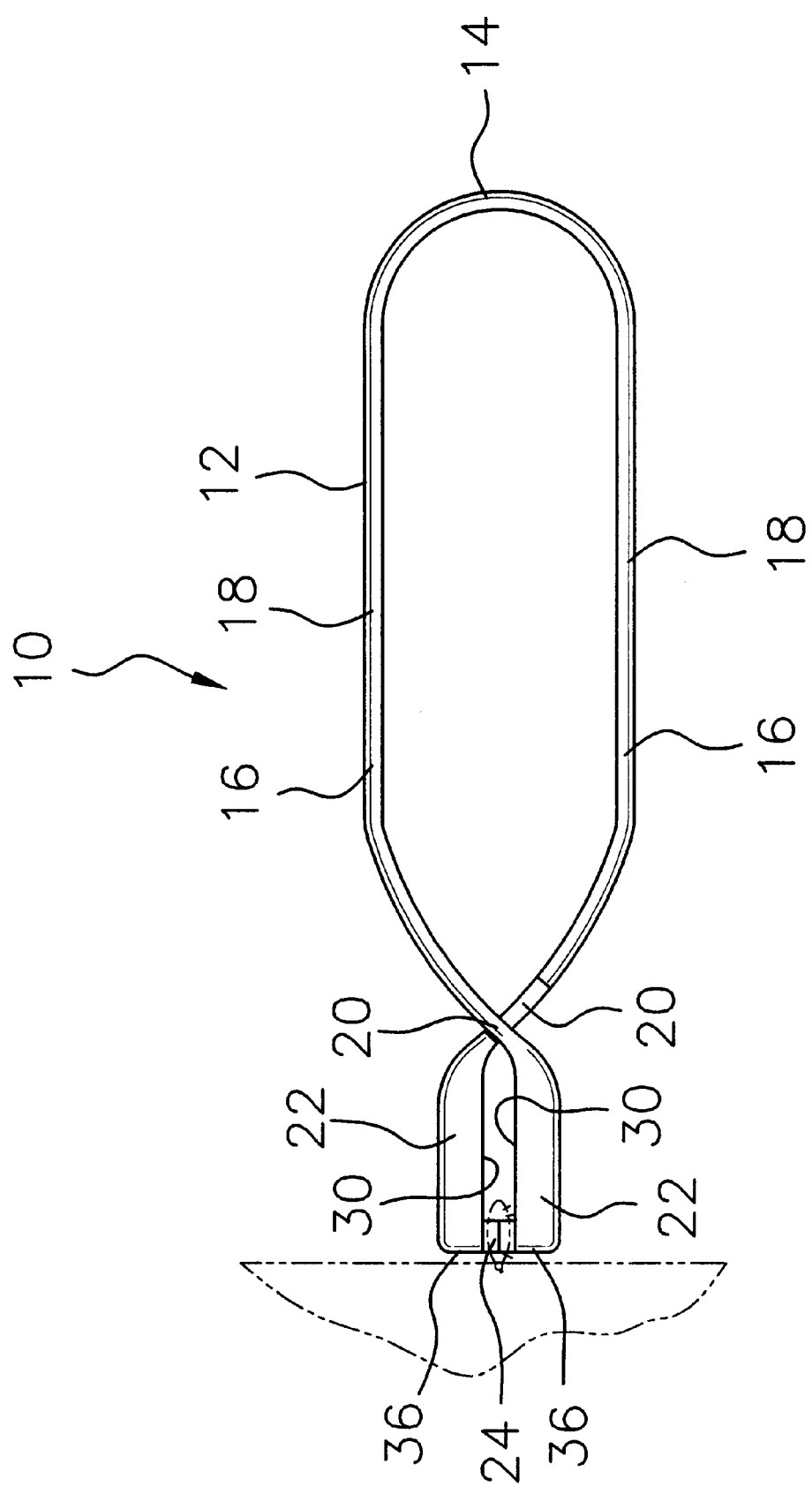
FIG. 1 is a side view of a new tick removing device according to the present invention.
Figure 2:
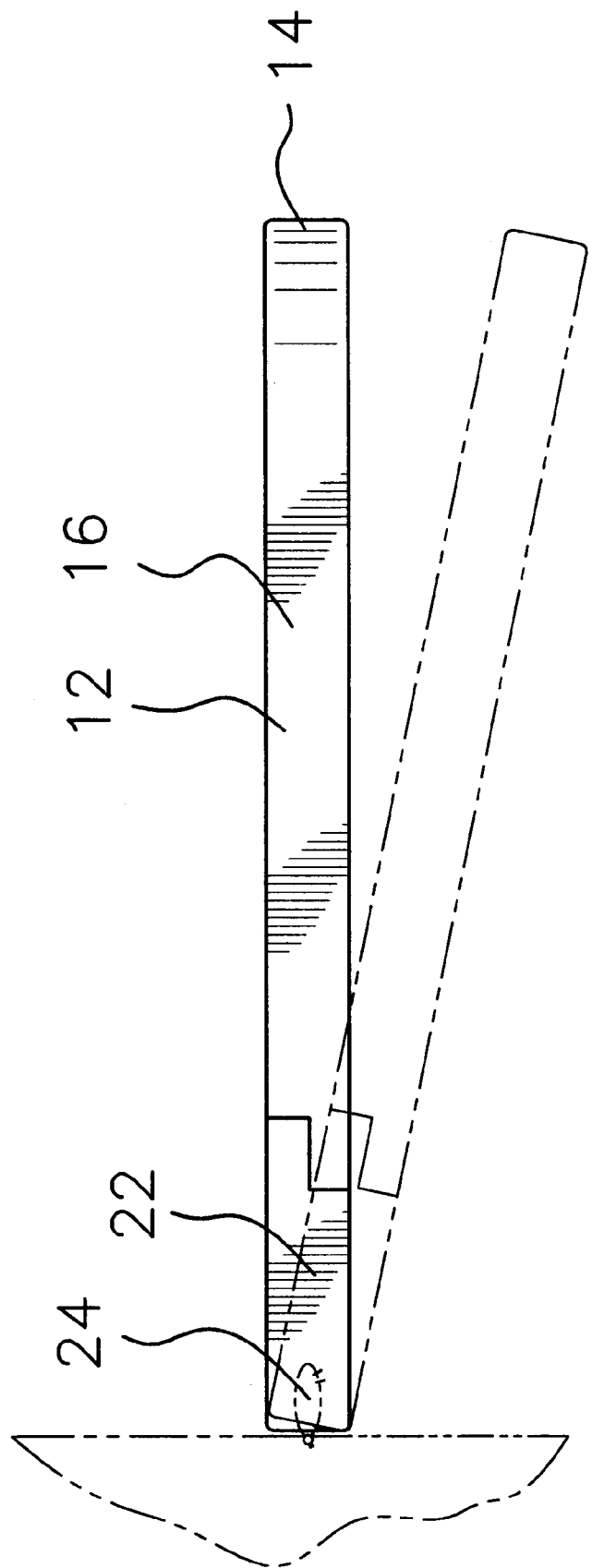
FIG. 2 is a top view of the present invention.
Figure 3:
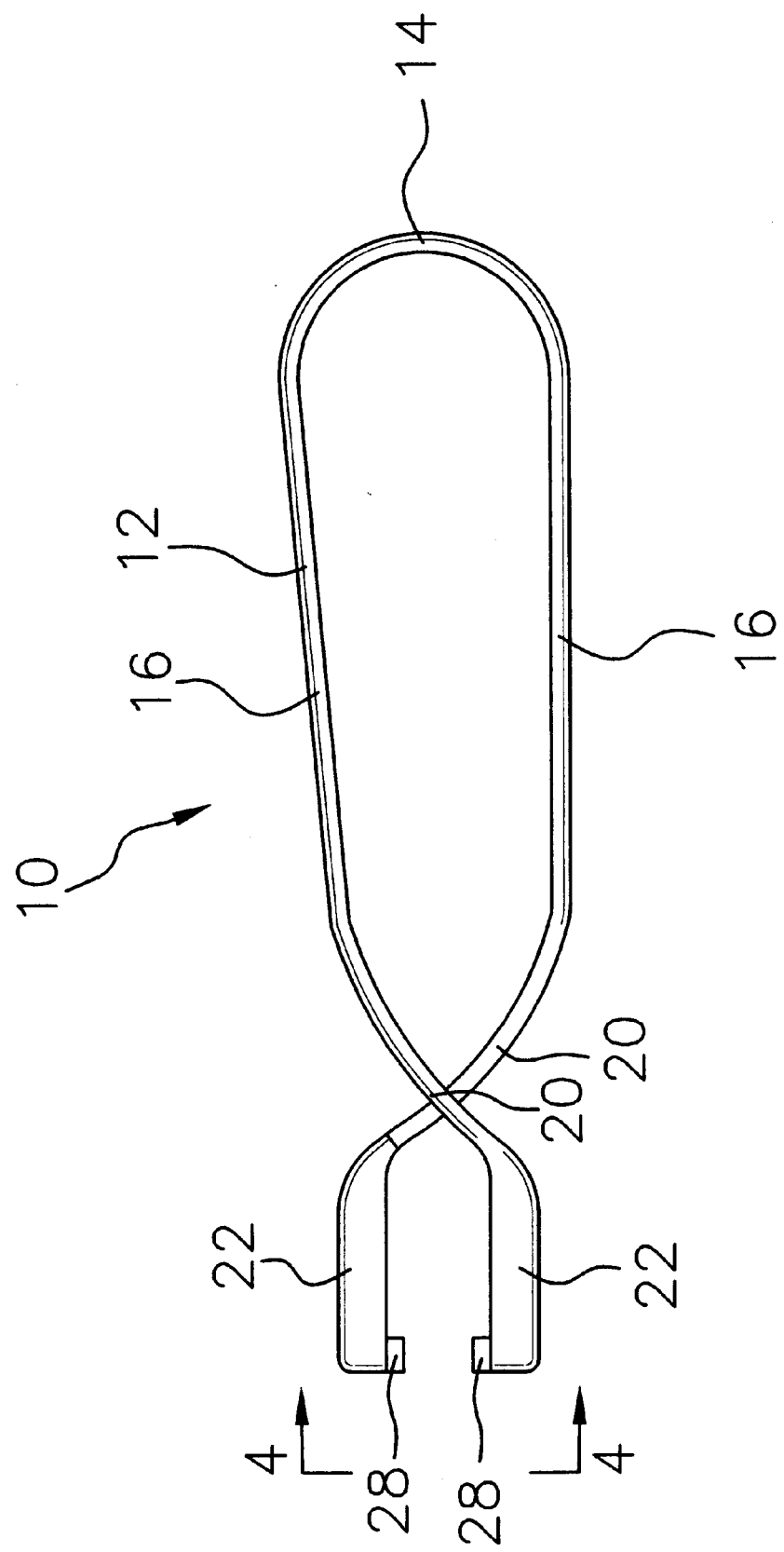
FIG. 3 is a side view of the present invention.

With reference now to the drawings, and in particular to FIGS. 1 through 4 thereof, a new tick removing device embodying the principles and concepts of the present invention and generally designated by the reference numeral 10 will be described.

As best illustrated in FIGS. 1 through 4, the tick removing device 10 generally includes a body member 12 that includes a fulcrum portion 14 and a pair arms 16. Each of the arms 16 has a main portion 18 that is coupled to the fulcrum portion 14. One of the arms 16 is positioned opposite from the other of the arms 16. The main portion 18 of each of the arms 16 is adapted for engaging a finger of a user. Each of the arms 16 has a free end 20. The free end 20 of one of the arms 16 crosses over the free end 20 of the other of the arms 16. Each of the arms 16 has a head portion 22. The head portion 22 of each of the arms 16 is adapted for engaging a portion of a body of the tick 24. A distance between the head portion 22 of each of the arms 16 increases when a gap between the main portions 18 of each of the arms 16 is decreased by pressure for the fingers of the user. The head portion 22 of one of the arms 16 abuts the head portion 22 of the other of the arms 16 when pressure from the fingers on the main portion 18 of each of the arms 16 is released such that the head portion 22 of each of the arms 16 is adapted for cooperatively securing the body member 12 to the tick 24 when the tick 24 is to be removed from the host.

The head portion 22 of each of the arms 16 has a gripping member 28. The gripping member 28 is coupled to an inner face 30 of the head portion 22 of each of the arms 16 such that the gripping member 28 of each of the arms 16 is adapted for gripping the body of the tick 24 from opposing sides for preventing slipping of the tick 24 within the head portion 22 of each of the arms 16 when the body member 12 is rotated for removing the tick 24 from the skin of the host.

The gripping member 28 of the head portion 22 of each of the arms 16 has an arcuate cut out 32. The arcuate cut out 32 is positioned adjacent to an interior face 34 of the gripping member 28. The arcuate cut out 32 is adapted for receiving a portion of the body of the tick 24 such that the arcuate cut out 32 prevents crushing of the tick 24 between the gripping member 28 of the head portion 22 of each of the arms 16 when the gripping member 28 of each of the arms 16 is secured to the tick 24.

The head portion 22 of each of the arms 16 has a substantially planar bottom face 36. The bottom face 36 of the head portion 22 of each of the arms 16 is adapted for abutting against the skin of the host such that the bottom face 36 of the head portion 22 of each of the arms 16 inhibits pinching of the skin of the host between the head portion 22 of the arms 16 when the user releases pressure from the main portion 18 of each of the arms 16.

In use, a user would squeeze the handle to force the tweezer ends apart. They could then be placed around and under the tick, and the handle would be released to allow the tweezer ends to close. The present invention could then be rotated counter-clockwise to force the tick completely off the skin.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A tick removing device for removing a tick from a skin of a host, the tick removing device comprising:

a body member comprising having a fulcrum portion and a pair arms, each of said arms having a main portion being coupled to said fulcrum portion such that one of said arms is positioned opposite from the other of said arms, said main portion of each of said arms being adapted for engaging a finger of a user, each of said arms having a free end, said free end of one of said arms crossing over said free end of the other of said arms;

each of said arms having a head portion, said head portion of each of said arms being adapted for engaging a portion of a body of the tick, a distance between said head portion of each of said arms increasing when a gap between said main portion of each of said arms is decreased by pressure for the fingers of the user, said head of one of said arms abutting said head portion of the other of said arms when pressure from the fingers on said main portion of each of said arms is released such that said head portion of each of said arms is adapted for cooperatively securing said body member to the tick when the tick is to be removed from the host; and said head portion of each of said arms having a substantially planar bottom face, said bottom face of said head portion of each of said arms being orthogonally positioned to a plurality of sides walls of the associated said head portion, said bottom face of said head portion of each of said arms being adapted for abutting against the skin of the host such that said bottom face of said head portion of each of said arms inhibits pinching of the skin of the host between said head portion of said arms when the user releases pressure from said main portion of each of said arms.

2. The tick removing device as set forth in claim 1, further comprising:

said head portion of each of said arms having a gripping member, said gripping member being coupled to an inner face of said head portion of each of said arms such that said gripping member of each of said arms is adapted for gripping the body of the tick from opposing sides for preventing slipping of the tick within said head portion of each of said arms when said body member is rotated for removing the tick from the skin of the host.

3. The tick removing device as set forth in claim 2, further comprising:

said gripping member of said head portion of each of said arms having an arcuate cut out, said arcuate cut out being positioned adjacent an interior face of said gripping member, said arcuate cut out being adapted for receiving a portion of the body of the tick such that said arcuate cut out prevents crushing of the tick between said gripping member of said head portion of each of said arms when said gripping member of each of said arms is secured to the tick.

4. A tick removing device for removing a tick from a skin of a host, the tick removing device comprising:

a body member comprising having a fulcrum portion and a pair arms, each of said arms having a main portion being coupled to said fulcrum portion such that one of said arms is positioned opposite from the other of said arms, said main portion of each of said arms being adapted for engaging a finger of a user, each of said arms having a free end, said free end of one of said arms crossing over said free end of the other of said arms; and each of said arms having a head portion, said head portion of each of said arms being adapted for engaging a portion of a body of the tick, a distance between said head portion of each of said arms increasing when a gap between said main portion of each of said arms is decreased by pressure for the fingers of the user, said head of one of said arms abutting said head portion of the other of said arms when pressure from the fingers on said main portion of each of said arms is released such that said head portion of each of said arms is adapted for cooperatively securing said body member to the tick when the tick is to be removed from the host;

wherein said head portion of each of said arms having a gripping member, said gripping member being coupled to an inner face of said head portion of each of said arms such that said gripping member of each of said arms is adapted for gripping the body of the tick from opposing sides for preventing slipping of the tick within said head portion of each of said arms when said body member is rotated for removing the tick from the skin of the host;

wherein said gripping member of said head portion of each of said arms having an arcuate cut out, said arcuate cut out being positioned adjacent an interior face of said gripping member, said arcuate cut out being adapted for receiving a portion of the body of the tick such that said arcuate cut out prevents crushing of the tick between said gripping member of said head portion of each of said arms when said gripping member of each of said arms is secured to the tick;

wherein said head portion of each of said arms having a substantially planar bottom face, said bottom face of said head portion of each of said arms being orthogonally positioned to a plurality of sides walls of the associated said head portion, said bottom face of said head portion of each of said arms being adapted for abutting against the skin of the host such that said bottom face of said head portion of each of said arms inhibits pinching of the skin of the host between said head portion of said arms when the user releases pressure from said main portion of each of said arms.

* * * * *